US005627038A

United States Patent [19]
Hemker

[11] Patent Number: 5,627,038
[45] Date of Patent: May 6, 1997

[54] FACTOR IX CHROMOGENIC ASSAY

[75] Inventor: H. C. Hemker, Maastricht, Netherlands

[73] Assignee: Dade International Inc., Deerfield, Ill.

[21] Appl. No.: 322,970

[22] Filed: Oct. 13, 1994

Related U.S. Application Data

[63] Continuation of Ser. No. 954,126, Jun. 3, 1992, abandoned, which is a continuation of Ser. No. 394,822, Aug. 17, 1989, abandoned.

[51] Int. Cl.$^6$ ................................................ G01N 33/53
[52] U.S. Cl. ...................... 435/7.21; 435/7.4; 435/13; 435/23; 435/24; 435/966; 435/975; 436/69; 436/808
[58] Field of Search ........................ 435/7.21, 7.4, 435/13, 23, 24, 810, 975, 966; 436/69, 808

[56] References Cited

U.S. PATENT DOCUMENTS

| | | | |
|---|---|---|---|
| 4,622,389 | 11/1986 | Nagasawa et al. | 530/331 |
| 5,059,525 | 10/1991 | Bartl et al. | 435/13 |

FOREIGN PATENT DOCUMENTS

| | | |
|---|---|---|
| 0241900 | 11/1985 | Japan . |
| 8800210 | 1/1988 | WIPO . |

OTHER PUBLICATIONS

Biological Abstract 62:000449 of Irwin et al, "Activation of factor IX by thrombin preparations in the absence of factor XI," Thromb. Res. 8(2):141–149 (1976).

Griffith et al. "Measurement of Human Factor IXa Activity In an Isolated Factor X Activation System," Thrombosis Research 27:289–301, (1982).

Jackson & Nemerson, "Blood Coagulation," in Annual Review of Biochemistry vol. 49, p. 768 (1980).

van Diejen-Visser et al. "Use of Chromogenic Peptide Substrates in the Determination of Clotting Factors II, VII, IX and X . . . " Haemostasis 12:241–255 (1982).

Biggs, Rosemary et al., "The Assay of Antihaemophilic–Globulin Activity," British Journal of Haematology, pp. 20–34.

Biggs, Rosemary, M.D. et al., "Christmas Disease A Condition Previously Mistaken for Haemophilia," British Medical Journal, Dec. 27, 1952, pp. 1378–1382.

Matchett, Myrtle O. et al., "Partial Thromboplastin Time Test With Kaolin", J. Clin. Path. (1965), 18, 465–471.

Morita, Takashi, et al., "New Fluorogenic Substrates for a-Thrombin Factor Xa, Kallikreins, and Urokinase", J. Biochem. 82, 1495–1498 (1977).

Pavlovsky, Alfredo, M.D., "Contribution to the Pathogenesis of Hemophilia", Division of Hematology of the Institute de Investigaciones Fisicas de la Academia Nacional de Medicina, Buenos Aires, Argentina.

Proctor, Robert R., et al., "The Partial Thromboplastin Time With Kaolin, A Simple Screening Test for First Stage Plasma Clotting Factor Deficiencies," The Amer. J. of Clin. Path., vol. 36, No. 3, pp. 212–219.

Sen, N. et al., "Modified Method for the Assay of Factor IX" from Medical Research Council, Blood Coagulation Research Unit, Churchill Hospital, Oxford.

Stuart, R., M.D. et al., "Monitoring Heparin Therapy With the Activated Partial Thromboplastin Time," Canadian Medical Association Journal, Mar. 6, 1971 vol. 104, No. 5.

(List continued on next page.)

Primary Examiner—Carol A. Spiegel
Attorney, Agent, or Firm—Cynthia G. Tymeson; Lois K. Winston

[57] ABSTRACT

A chromogenic assay for determination of blood coagulation Factor IX (christmas factor) utilizes Factor Xa formed by the conversion of Factor X by activated Factor IX and Factor VIII to cleave a chromogenic substrate. The sample is combined into a mixture with Factor XIa in the presence of Factor IIa (thrombin), incubated, combined with Factor X and Factor VIII, and incubated. A thrombin inhibitor, and an indicator agent which reacts with Factor Xa, are added and the resulting signal measured and correlated to the level of Factor IX in the sample.

16 Claims, 3 Drawing Sheets

1) Factor IX  $\xrightarrow{\text{Factor XIa, Ca}^{++}, \text{Factor IIa}}$  Factor IXa 2) Factor X  $\xrightarrow{\text{Factor IXa, Phospholipid, Factor VIIIa, Ca}^{++}}$  Factor Xa 3) Indicator Agent + Thrombin Inhibitor  $\xrightarrow{\text{Factor Xa}}$  signal molecule

OTHER PUBLICATIONS

Svendsen, L., et al., "Differentiation of Thrombin–and Factor Xa–Related Amidolytic Activity in Plasma by Means of a Synthetic Thrombin Inhibitor" Thrombosis Research 34:457–462, 1984.

Van Dieijen–Visser, "Use of Chromogen ic Peptide Substrates in the Determination of Clotting Factors II, VII, IX and X in Normal Plasma and in Plasma of Patients Treated with Oral Anticoagulants", Haemostasis 12:241–55 (1982).

Byrne, et al., "Ion Specificity of the Conversion of Bovine Factors IX, IXa, and IXaa to Bovine Factor IXaB" J. Bio. Chem. 25:1439–1435 (1980).

Enfield, et al., "Cleavage and Activation of Human Factors IX by Serine Proteases", Blood 64:821–831 (1984).

Griffith, et al., "Measurement of Human Factor IXa Activity in an Isolated Factor X Activation System", Throm. Res. 27:289–301.

Mertens, et al., "The Contribution of Ca2+ and Phospholipids to the Activation of Human Blood–Coagulation Factor X by Activated Factor IX·m H", Biochem. 223(3):607–15 (1984).

Silverberg et al., "Kinetics of Activation of Bovine Coagulation Factor X by Components of the Extrinsic Pathway" J. Biol. Chem. V.252:8481–8488 (1977).

Tans et al., "Activation of Factor XIa–A Spectrophotometric Assay for Factor IX in Human Plasma", Thromb. Haemostas 48:127–132 (1972).

Wagenvoord R, Hendrix H, and Hemker H, "Development of a simple factor VIII Assay for clinical use" (Abstract); Thrombosis Haemostasis; 58:p. 341 (1987).

FACTOR IX CHROMOGENIC ASSAY

This is a continuation of application Ser. No. 07/954,126, filed on Jun. 3, 1992, now abandoned, which is a continuation of application Ser. No. 07/394,822, filed on Aug. 17, 1989 now abandoned.

FIELD OF THE INVENTION

This invention relates generally to the field of chromogenic assays and more specifically to chromogenic assays for the determination of levels of blood coagulation factors contained in plasma and other fluids.

BACKGROUND OF THE INVENTION

Haemophilia is a sex-linked disease caused by a deficiency in certain circulating blood clotting factors. Haemophilia A is one such disease associated with a deficiency in coagulation Factor VIII. Haemophilia B is another such disease resulting from a deficiency in the levels of coagulation Factor IX. Haemophilia B is five to seven times less common than Haemophilia A, and is transmitted in humans as a chromosome X-linked recessive trait. Accordingly, occurrence of the disease is almost exclusively in males who receive the defective gene from their carrier mothers.

Although any individual having the defective genotype for Haemophilia B will be deficient in serum Factor IX, such individuals will vary greatly in the severity of the deficiency. Clinically, any individual having serum deficiency in Factor IX five to twenty-five percent (5–25%) of the levels typically observed in normal serum are classified as mild cases. Those individuals having deficiencies one to five percent (1–5%) of normal are considered moderate, and those having deficiencies less than one percent (1%) are considered severe cases. Approximately twenty to fifty percent (20–50%) of normal Factor IX levels is required for minimal hemostasis. Below this range there is a tendency to hemorrhage, with more severe bleeding being life threatening. It is therefore important clinically to be able to monitor accurately the levels of serum Factor IX in Haemophilia A patients, so as to timely implement appropriate therapy.

Other medical conditions exist which require accurate Factor IX determinations. Certain drug therapy, for example, warfarin treatment, is known to influence Factor IX levels. Also patients suffering from consumptive coagulopathies such as thrombosis or disseminated intravascular coagulation (DIC) may present anomalies in Factor IX levels which require careful clinical management. Successful treatment of these conditions similarly requires accurate determination of serum Factor IX levels. For a general review of the physiological and biochemical aspects of Factor IX deficiency diseases in relation to normal blood clotting see R. Coreman, Ed., *Hemostasis and Thrombosis: Basic Principles and Clinical Practice*, 2e Ed., Lippincott, Pa. 1989.

In managing any of the aforementioned medical conditions, one mode of treatment involves administration of exogenous Factor IX obtained by fractionation of whole blood plasma, utilizing techniques well-known to those experienced in the art. Factor IX obtained by such techniques is ordinarily concentrated so as to be administered in a convenient-size dose. It is essential that the precise concentration of such therapeutic doses be measured, and the quantity of Factor IX be carefully monitored at each step of the purification process.

Accordingly, there are available in the prior art, methods for the quantitative determination of blood coagulation Factor IX. The most significant method, which has become the standard assay in this field, is known as the Activated Partial Thromboplastin Time (APTT). In this method, the percent of Factor IX present in a test sample is determined by the degree of correction obtained when the plasma is added to a Factor IX deficient plasma. The degree of correction is determined by activated partial thromboplastin time. Results are compared to the degree of correction obtained when dilutions of normal plasma are added to the Factor IX deficient reference plasma.

In the APTT assay, according to Matchett and Ingram, *Partial Thromboplastin Time Test with Kaolin*, J. Clin. Path., 18:465 (1965), a plasma sample is incubated in a buffered solution containing Kaolin to which is then added a suspension of inosithin. The clotting time is measured and the data is plotted against a standard curve.

The method of the prior art has been studied and improved many times and may be conducted in either one or two stages. However, all the variations in method have the disadvantage of high variability in results, particularly in low level determination of Factor IX. This lack of sensitivity and reproducibility occurs at the very levels of detection when accuracy is most crucial.

Another major disadvantage of the APTT method is that drugs such as heparin interfere with the assay leading to false or misleading results. Still further disadvantages include the requirement for large quantities of Factor IX deficient plasma, which is difficult and expensive to procure, and the difficulty in automating the procedures. Finally, the APTT and related methods are not specific for Factor IX, but are applicable to the assay of several blood clotting factors. All such assays rely upon the presumption that "normal" plasma will give a one hundred percent (100%) correction in thromboplastin time. This means that persons performing the assay are subjected to the inconvenience of constructing a standard curve each time the assay is run.

SUMMARY OF THE INVENTION

This invention provides a highly sensitive, reproducible, and convenient assay for determination of the levels of blood coagulation Factor IX contained in blood serum, plasma, and other fluids. In the assay of this invention, a test sample of blood serum, plasma, or other Factor IX-containing fluid is added to a solution containing activated blood coagulation Factor XI, (referred to hereafter as Factor XIa), calcium ions and thrombin (Factor IIa). After a period of incubation during which the Factor IX is converted substantially completely to activated Factor IX, (hereafter referred to as Factor IXa), a second solution containing blood coagulation Factors VIII, X, phospholipids and calcium ions is added to the incubation mixture and further incubated. During this incubation Factor VIII is converted to Factor VIIIa and Factor IXa, produced during the first incubation, act to accelerate the conversion of the Factor X to activated Factor X, (hereafter referred to as Factor Xa). The rate Factor Xa is produced in this reaction is directly proportional to the amount of Factor IXa formed. An indicator agent is added to the reaction mixture, which reacts with the Factor Xa so formed, to release a signal molecule, which may be conveniently measured. The steps of the present invention are illustrated in FIG. 1.

In accordance with the method of this invention, an assay is provided which has a high degree of sensitivity and reproducibility, particularly in the lower ranges of Factor IX concentration. Another object of this invention is to provide a kit for the convenient performance of routine laboratory assays of Factor IX-containing fluids. A further object of this invention is to provide an assay for Factor IX which is not affected by the presence of heparin and other blood clot interactive substances. A still further object of this invention is to provide a bulk source of assay components to facilitate the operation of automated equipment capable of processing for assay large numbers of test samples.

The advantages and performance of the present invention will be better understood by reference to the following detailed description and Example.

DETAILED DESCRIPTION OF THE PREFERRED EMBODIMENT

The method of the assay of the present invention comprises the steps of:

1. Combining into a mixture a fluid sample containing a known or unknown amount of Factor IX with Factor XIa in the presence of calcium ions ($Ca^{++}$) and thrombin;
2. Incubating the mixture for a time sufficient to convert substantially all of the Factor IX to Factor IXa;
3. Further combining the incubation mixture with Factor X in the presence of phospholipids, factor VIII, and calcium ions ($Ca^{++}$);
4. Incubating the mixture for a time sufficient to convert all or a portion of the Factor X to Factor Xa;
5. Adding to the incubation mixture an indicator agent capable of reacting with Factor Xa, whereby to release a signal molecule; and
6. Measuring the signal molecule.

Figure 1:
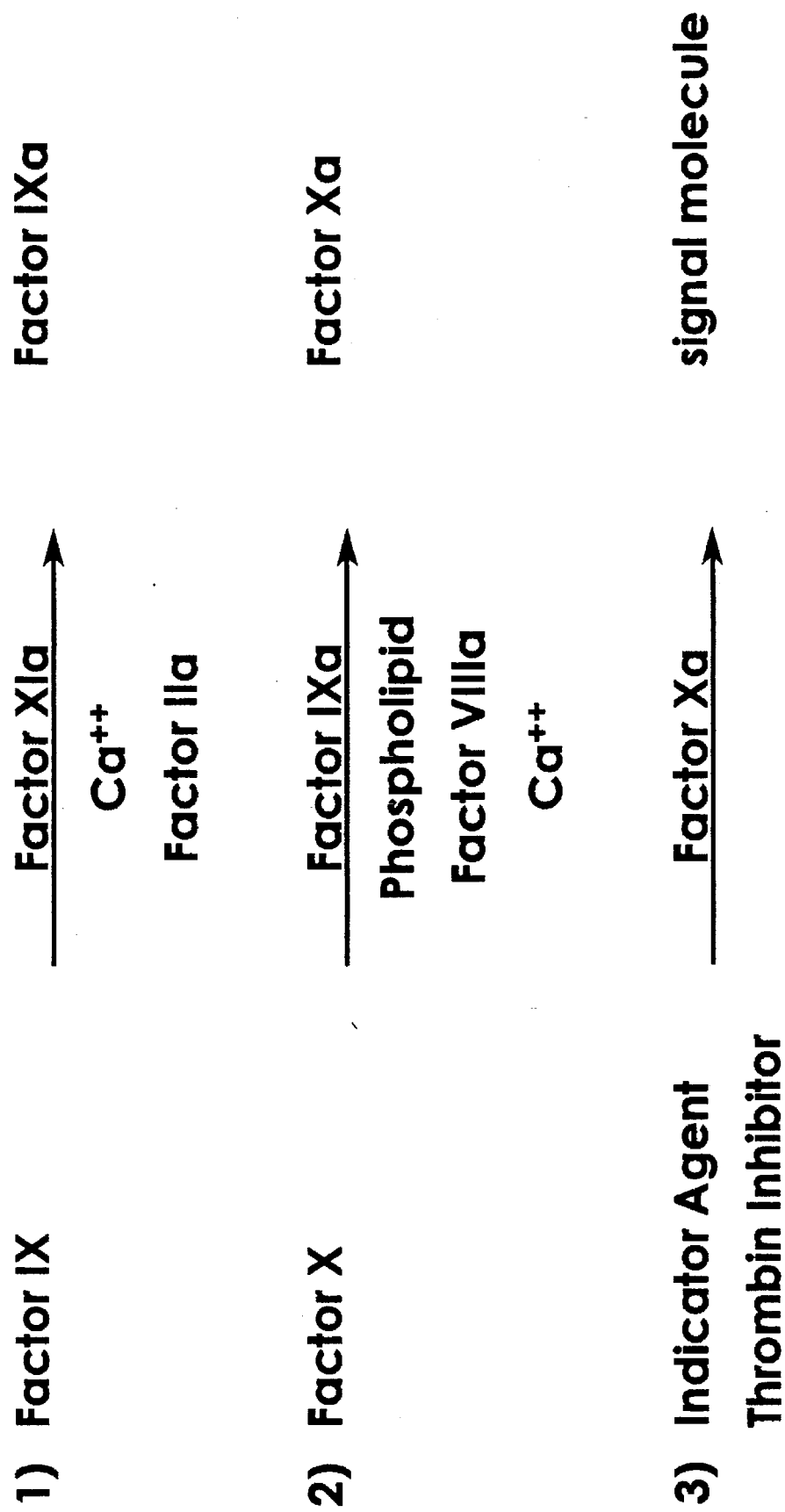
FIG. 1 describes the chemical equations illustrating the steps of the present method.

The foregoing method may conveniently be defined by reference to FIG. 1.

In practicing the method of the present invention, Factors XI, VIII, IIa and X may be obtained from virtually any animal or human source, and may be prepared by any fractionation or concentration method known to the art. In addition, a highly purified source of such factors is from recombinant vectors propagated in suitable host cell lines. One advantage to using factors from animal or recombinant vector sources is assurance that the product factors will not be contaminated with human pathogens such as hepatitis A and B, HTLV-III, or other such viruses. In the preferred embodiment of the present method, blood coagulation factors are of bovine origin.

The conversion of Factor X to Xa proceeds most efficiently in the presence of phospholipids. These phospholipids may be such representative compounds as phosphotidyl choline, phosphotidyl serine, or cholesterol and mixtures thereof in various proportions. Other lipid and phospholipid compositions may be substituted as well, but the preferred phospholipid composition consists of about 60% phosphotidyl choline, 23% phosphotidyl serine, and 8% cholesterol.

Any chemical source of calcium cation may be used to effectuate the conversion of Factors X and XI. Sufficient calcium ion may be added to the original incubation mixture to drive the reaction converting Factor X to Factor Xa, or a second amount of calcium ion may be added at the time Factor X is to be converted. While the source of calcium cation ($Ca^{++}$) may be $CaCl_2$, $Ca(NO_2)_2$, $CaSO_4$, or other inorganic or organic calcium cation containing compounds, the preferred source is $CaCl_2$.

In performing the assay of this invention, a great variation in protein concentrations, incubation times, reagent concentrations, and temperatures may be employed. The selection of particular assay parameters will be influenced by the source, type, and size of the sample to be assayed, the anticipated levels of Factor IX contained therein, and the threshold of sensitivity desired. Taking these circumstances into account, selection of assay parameters will be apparent to those skilled in the art. The parameters of the assay, which will enable anyone skilled in the art to carry out the assay in accordance with a preferred embodiment are set forth in the Example which follows.

Since the level of Factor IX present in a test sample is proportional to the rate at which the Factor X is converted to Factor Xa, it is advantageous to perform this assay by measuring the signal molecule released from the indicator agent at some fixed point in time after commencement of the reaction. Accordingly, an optional additional step in the present assay consists of adding a quenching composition to the incubation mixture at a fixed point in time after commencement of the reaction converting Factor X to Factor Xa. The quenching composition may be any substance capable of disrupting a protein-mediated chemical reaction, but the preferred composition is a buffered solution comprised of Tris, ethylenediaminetetracetic acid, sodium chloride, and sodium azide. Concentrations of said ingredients in the preferred composition are set forth in the Example.

The blood coagulation factors of the present assay and the Factor IX protein to be assayed are fragile functional proteins, and desirably a stabilizing substance or substances may be included during the incubation to optimize assay conditions and to protect functionality of assay components. Such stabilizing substances also protect functionality during storage wherein the assay components are maintained in either a wet or lyophilized state. Various stabilizers are known in the art; the preferred substances being polyethylene glycol and bovine serum albumin, either singly or in combination.

Figure 2:
FIG. 2 describes the chemical equation illustrates the conversion of a chromogenic compound by Factor Xa to produce a signal molecule.

The indicator agent of the present invention is a molecule capable of reacting with blood coagulation Factor Xa. In such reaction, by-products of chemical reaction must be generated which produce a measurable signal moiety. U.S. Pat. Nos. 4,480,030 and 4,666,831 describe a class of chromogenic compounds capable of reacting with Factor Xa. The preferred member of this class of compounds, particularly suitable in the present assay, reacts with Factor Xa according to the equation in FIG. 2. Upon reaction with Factor Xa, a signal molecule P-nitroaniline is released, which may be conveniently measured by spectrophotometric determination at 405 nm.

Other chromogenic indicator agents which are applicable with the present invention are available also. From the preceding disclosure it will be apparent to those skilled in the art that the signal moiety of the target indicator agent may be radiolabelled, preferably by tritium or carbon 14, and the signal molecule upon release can be isolated as by gel exclusion chromatography, dialysis, immunoadsorption, or other convenient separation techniques. Radiolabelled indicator agents, while more cumbersome to use, have the advantage of greater sensitivity in those situations wherein unusually great sensitivity is needed.

A thrombin inhibitor can be included with the indicator agent preparation. A chemical name of a thrombin inhibitor is Nα-(2-Naphthylsulfonylglycyl)-D,L-amidinophenylalanine-piperide (α-NAPAP).

It is contemplated within the scope of the present invention that the components of the Factor IX assay be may available as a kit for the convenient and routine performance of a large number of such assays. The assay kit comprises a vessel containing Factor XIa in a quantity sufficient for one or a plurality of Factor IX assays, a second vessel containing Factors VIII and X in a quantity sufficient for one or a plurality of Factor IX assays, a third vessel containing an indicator agent in a quantity sufficient for one or a plurality of Factor IX assays, and optionally, a fourth vessel containing a quenching composition in a quantity sufficient for one or a plurality of Factor IX assays. To optimize shelf life of the components of the kit it is desirable to lyophilize them in the aforementioned vessels. The said components may be readily reconstituted by adding water at the time assays are to be performed. The vessels containing assay components are readily adapted to automated assay equipment.

Further advantageous aspects of the present invention will be apparent from the following Example.

EXAMPLE

Patient samples were prepared by adding to nine parts freshly drawn blood to one part 0.13M sodium citrate, followed by centrifugation for ten minutes at about 3000 rpm.

Patient plasma samples were added to a water reconstituted lyophilized preparation containing 4.5 pmol of bovine Factor XIa, 0.2 nmol bovine thrombin, 0.06 nmol calcium chloride, 0.06 umol phospholipids, tris-(hydroxymethyl)-aminomethane (Tris) buffer at pH 8, and stabilizers BSA and polyethylene glycol 6000. Incubation was subsequently carried out alternatively at 25° C., 30° C., and 37° C. for approximately ten minutes.

After incubation, a water reconstituted lyophilized preparation containing approximately 1 mmol bovine Factor X, approximately three units bovine Factor VIII, and Tris buffer pH 8 was added to the incubation mixture. After ten minutes, a water reconstituted lyophilized indicator agent preparation containing 3.4 umol $CH_3$-OCO-d-CHG-Gly-Arg-pNA, a thrombin inhibitor, and protein stabilizers was added. Reaction was terminated by addition of a quenching substance comprising Tris buffer (20 mM), ethylenediaminetetracetic acid (10 mM), sodium chloride (5 mM), and sodium azide (0.01M). Determination of spectrophotometric adsorption at 405 nm was made on a Beckman 2D spectrophotometer.

Plasma samples from 103 patients are analyzed for Factor IX content. Many of these patients were known hemophiliacs, and some were undergoing therapy with various drugs known to interfere with classical assays of the prior art.

Figure 3:
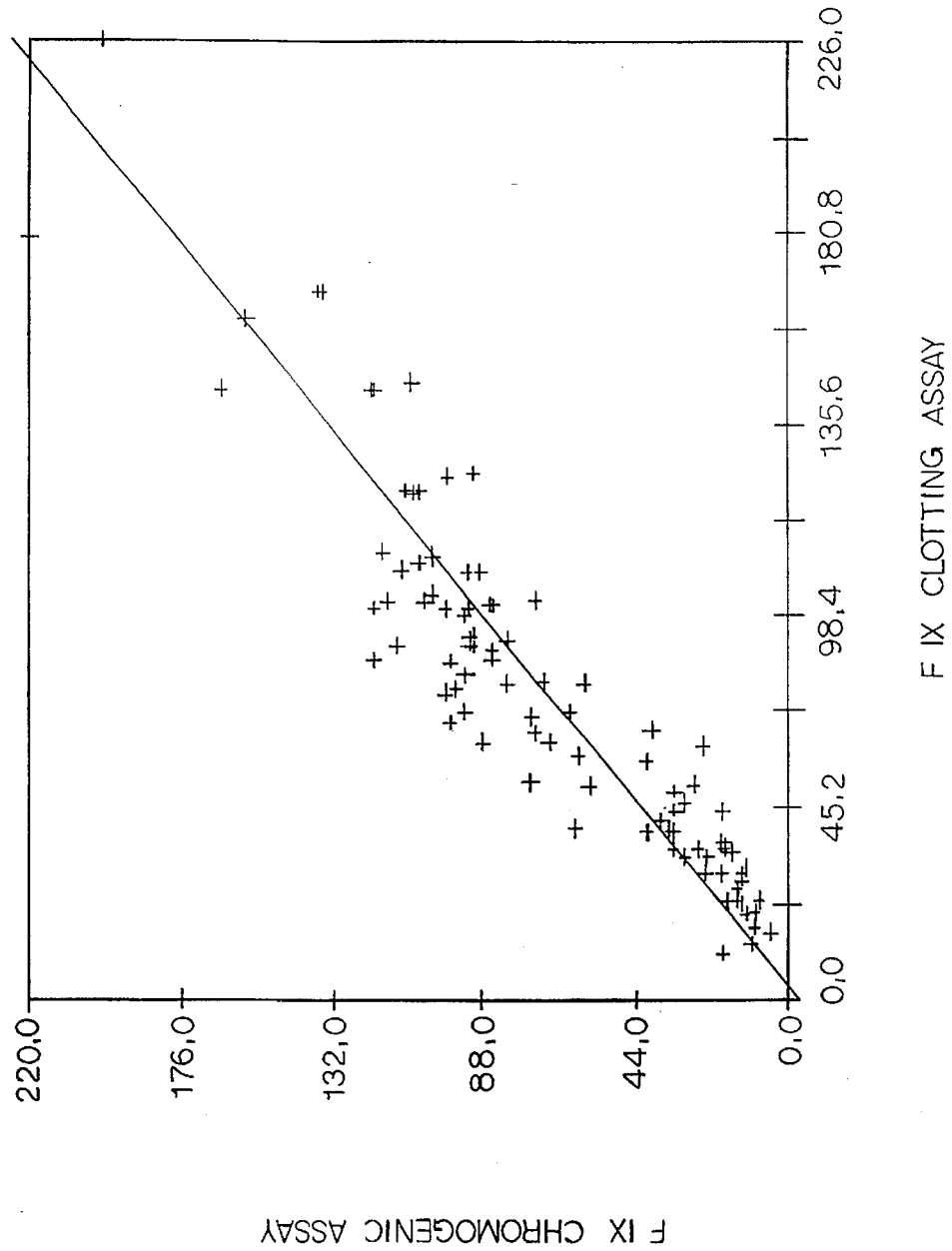
FIG. 3 is a graph of a comparison study of split samples assayed by the method of the present invention and a prior art assay.

The results indicate that the presence of heparin in the plasma of patients undergoing heparin therapy did not interfere with the assay of the present invention. The invitro adding of up to 3 U/ml heparin to plasma had no significant effect on the assay. Further, as shown in FIG. 3, there was highly significant correlation of Factor IX values in a comparative study of split samples tested by the new assay and the assay of the prior art: N=98, r=0.94 and Y=0.97, and N=98, r=0.93 and y=1.01 x+3 at two different trial sites.

What is claimed is:

1. A method for determining coagulation Factor IX in a blood, serum, plasma or other fluid sample suspected of containing Factor IX comprising:

a) combining into a mixture said fluid sample with blood coagulation Factor XIa in the presence of calcium ions and Factor IIa;

b) incubating the mixture for a time sufficient to convert substantially all of the Factor IX to Factor IXa;

c) further combining the mixture with Factor X in the presence of phospholipids, Factor VIII and calcium ions;

d) incubating the mixture for a time sufficient to convert all or a portion of the Factor X to Factor Xa;

e) adding to the mixture a Factor IIa inhibitor and an indicator agent capable of reacting chemically with the Factor Xa to generate a measurable signal;

f) measuring the signal; and g) correlating the measured signal molecule to the level of blood coagulation Factor IX in the fluid sample.

2. The method of claim 1 further comprising adding a quenching composition between steps d) and e) to stop any further conversion of the Factor X to the Factor Xa, thereby providing a predetermined amount of Factor Xa.

3. The method of claim 1 wherein said Factors IIa, XIa, VIII, and X are obtained from an animal source.

4. The method of claim 1 wherein said Factors IIa, XIa, VIII, and X are recombinant.

5. The method of claim 1 wherein the Factor IIa inhibitor is N alpha-(2-Naphthylsulfonylglycyl)-D,L-amidophenylalanine-piperide.

6. The method of claim 1 wherein the measurable signal is p-nitroaniline.

7. The method of claim 1 further comprising adding said Factor IIa inhibitor simultaneously with the indicator agent of step e) to inhibit further conversion of the Factor VIII to Factor VIIIa by Factor IIa.

8. The method of claim 2 wherein said Factors IIa, XIa, VIII, and X are obtained from an animal source.

9. The method of claim 2 wherein said Factors IIa, XIa, VIII, and X are recombinant.

10. The method of claim 2 wherein the Factor IIa inhibitor is N alpha-(2-Naphthylsulfonylglycyl)-D,L-amidophenylalanine-piperide.

11. The method of claim 2 wherein the measurable signal is p-nitroaniline.

12. A kit for performing a Factor IX assay in a blood, serum, plasma or other fluid sample suspected of containing said Factor IX comprising:

a) a vial containing Factor XIa and Factor IIa;

b) a second vial containing Factors VIII and X; and c) a third vial containing a Factor IIa inhibitor and an indicator agent capable of reacting chemically with Factor Xa to produce a measurable signal.

13. A kit for performing a Factor IX assay in a blood, serum, plasma or other fluid sample suspected of containing Factor IX comprising:

a) a vial containing Factor XIa and Factor IIa;

b) a second vial containing Factors VIII and X;

c) a third vial containing a Factor IIa inhibitor and an indicator agent capable of reacting chemically with Factor Xa to produce a signal molecule; and d) a fourth vial containing a quenching composition to stop conversion of said Factor X to Factor Xa.

14. The kit of claim 12 or 13 wherein said Factors VIII, X, and XIa are obtainable from an animal source.

15. The kit of claim 12 or 13 wherein said Factors VIII, X, and XIa are recombinant.

16. The kit of claim 12 or 13 wherein the Factor IIa inhibitor is N-alpha-(2-Naphthylsulfonylglycyl)-D,L-amidophenylalaninepiperide.

* * * * *